(12) United States Patent
Anderson et al.

(10) Patent No.: US 9,675,776 B2
(45) Date of Patent: Jun. 13, 2017

(54) MULTI-SENSORY THERAPEUTIC SYSTEM

(71) Applicant: THE BLOCK SYSTEM, INC., Fort Worth, TX (US)

(72) Inventors: Joan Anderson, Fort Worth, TX (US); Mary Ann Block, Fort Worth, TX (US)

(73) Assignee: The Block System, Inc., Fort Worth, TX (US)

( * ) Notice: Subject to any disclaimer, the term of this patent is extended or adjusted under 35 U.S.C. 154(b) by 525 days.

(21) Appl. No.: 14/159,286

(22) Filed: Jan. 20, 2014

(65) Prior Publication Data

US 2014/0206929 A1 Jul. 24, 2014

Related U.S. Application Data

(60) Provisional application No. 61/754,636, filed on Jan. 20, 2013.

(51) Int. Cl.
| | | |
|---|---|---|
| *A61M 21/00* | (2006.01) | |
| *A61G 7/05* | (2006.01) | |
| *A61G 15/02* | (2006.01) | |

(52) U.S. Cl.
CPC ............ *A61M 21/00* (2013.01); *A61G 7/0503* (2013.01); *A61G 15/02* (2013.01); *A61M 2021/0005* (2013.01); *A61M 2021/0022* (2013.01); *A61M 2021/0027* (2013.01); *A61M 2021/0044* (2013.01); *A61M 2205/505* (2013.01)

(58) Field of Classification Search
CPC .... A61B 3/0083; A61G 15/02; A61G 15/007; A61M 2021/0005; A61M 2021/0011; A61M 2021/0033; A61M 2021/0038
See application file for complete search history.

(56) References Cited

U.S. PATENT DOCUMENTS

| | | | |
|---|---|---|---|
| 3,524,676 A | 8/1970 | Cocherell et al. | |
| 3,628,829 A | 12/1971 | Heilig | |
| 4,315,502 A | 2/1982 | Gorges | |
| 4,690,142 A | 9/1987 | Ross et al. | |
| 4,728,293 A | 3/1988 | Kole, Jr. | |
| 5,047,006 A * | 9/1991 | Brandston ............. | A61M 21/00 250/228 |
| 5,304,112 A | 4/1994 | Mrklas et al. | |

(Continued)

OTHER PUBLICATIONS

Sensory Training—SIRRI SenEx™, <http://www.sirrisenex.com/what_senex_is.shtml>, captured Oct. 20, 2014.

(Continued)

*Primary Examiner* — Charles A Marmor, II
*Assistant Examiner* — Shannon McBride
(74) *Attorney, Agent, or Firm* — Roberts Foster LLP (57) ABSTRACT

A system for providing multi-sensory therapy including a computer having an audio output and a screen, wherein the computer is configured to provide audio stimulus and visual stimulus, a motion chair, and an actuator coupled to the motion chair, wherein the actuator is configured to cause movement of the motion chair, wherein the motion of the motion chair is configured to provide tactile stimulus, vestibular stimulus and proprioceptive stimulus to a patient seated in the motion chair, wherein the stimuli provided by the computer is provided concurrently with the stimuli provided by the motion chair.

6 Claims, 6 Drawing Sheets

(56) References Cited

U.S. PATENT DOCUMENTS

| | | | |
|---|---|---|---|
| 5,913,310 | A | 6/1999 | Brown |
| 6,651,279 | B1 | 11/2003 | Muthuvelan |
| 6,656,137 | B1 | 12/2003 | Tyldsley et al. |
| 6,695,779 | B2 | 2/2004 | Sauer et al. |
| 6,702,767 | B1 | 3/2004 | Douglas et al. |
| D597,677 | S | 8/2009 | Steinert |
| 8,265,746 | B2 | 9/2012 | Chan et al. |
| 2002/0138441 | A1 | 9/2002 | Lopatic |
| 2002/0183667 | A1 | 12/2002 | Kitadou et al. |
| 2006/0058701 | A1 | 3/2006 | Bolles et al. |
| 2006/0206175 | A1 | 9/2006 | Fernandez Tournier et al. |
| 2007/0100214 | A1 | 5/2007 | Steinert |
| 2009/0240172 | A1 | 9/2009 | Fernandez Tournier et al. |
| 2010/0312041 | A1* | 12/2010 | Elliott .................... A61B 5/486 600/27 |
| 2011/0028872 | A1 | 2/2011 | Kevin |
| 2011/0251535 | A1 | 10/2011 | Bender |
| 2012/0294451 | A1* | 11/2012 | Kozuka ................. H04R 25/70 381/60 |
| 2013/0090520 | A1* | 4/2013 | Redfield ............... A61M 21/00 600/28 |

OTHER PUBLICATIONS

SIRRI Center, (for brain-based disorders), <http://cpfamilynetwork.org/cerebralpalsyresources/ny/plain-view/sirri-center-brain-based-disorders>, published Apr. 14, 2012, captured Oct. 20, 2014.
Sensory Learning Program, <http://www.sirri.com/sensory_learning/index.shtml>, captured Oct. 20, 2014.
The Sound Learning Centre—Treatment, <http://www.thesoundlearningcentre.co.uk/treatment>, captured Oct. 20, 2014.
Sensory Learning, <http://sensoryleaning.com/program.php>, captured Oct. 20, 2014.

* cited by examiner

MULTI-SENSORY THERAPEUTIC SYSTEM

CROSS-REFERENCE TO RELATED APPLICATION

This application claims the benefit of U.S. provisional patent application Ser. No. 61/754,636 filed Jan. 20, 2013, and entitled "Multi-Sensory Therapeutic System," which is hereby incorporated herein by reference in its entirety.

STATEMENT REGARDING FEDERALLY SPONSORED RESEARCH OR DEVELOPMENT

Not applicable.

BACKGROUND

Sensory processing disorder (SPD) is a neurological disorder affecting one's ability to receive, process and respond to sensory stimuli from the surrounding environment and one's own body (e.g., visual, auditory, tactile, vestibular and proprioceptive). First studied in-depth by occupational therapist Anna Jean Ayers (then known as sensory integration dysfunction), Ayers described sensory integration as the neurological process that organizes sensations from one's own body and from the surrounding environment, making it possible to use the body effectively within the environment. Thus, one afflicted with SPD may have a reduced ability to organize and process sensory stimuli.

Unlike hearing or visual impairment, those suffering from SPD have the ability to perceive stimuli but register and process the received stimuli differently in the brain. For instance, one suffering from SPD may have the ability to "hear" or perceive sounds but lack the ability to "listen" or mentally digest and process the perceived sound in the brain. Further, delayed sensory development may also result from SPD, resulting in slow vision processing and reading abilities. For example, someone suffering from SPD may have a reduced visual field, leading to a reduction in the volume of information that may be processed through the eyes, which may in turn affect the person's academic achievement, work proficiency and athletic capabilities.

SPD may be broken down into three primary diagnostic groups including Sensory Modulation Disorder (SMD), Sensory Based Motor Disorder (SBMD) and Sensory Discrimination Disorder (SDD), with each diagnostic group exhibiting a particular set of symptoms. For instance, SMD is associated with over or under responding to sensory stimuli, SBMD is associated with disorganized motor output resulting from difficulty in processing sensory information and SDD is associated with sensory discrimination (e.g., inattentiveness, disorganization, etc.). SPD also shares relationships with other neurological disorders, such as autism spectrum disorders, which is a common comorbidity with SPD.

Sensory integration therapy was developed as a means for treating SPD and includes sensory stimulation or inhibition targeted at the tactile, vestibular, proprioceptive, visual and auditory systems. However, currently developed sensory integration therapies may not fully take advantage of the benefits provided by sensory integration. For example, current techniques may fail to stimulate each of the five aforementioned sensory systems concurrently, thus failing to fully integrate the sensory stimuli and in turn reducing the effectiveness of the sensory integration therapy. Due to the type of equipment used, there may also be errors or other issues in the delivery of the sensory stimulation to the patient. Therefore, there is a need in the art for systems and methods of multi-sensory or sensory integration therapy that provides more effective sensory stimuli to the patient. Also, it would be beneficial if such systems and methods more effectively and intensely integrate different forms of sensory stimuli as they are provided to the patient.

BRIEF SUMMARY OF THE DISCLOSURE

The embodiments described herein are generally directed towards a system for providing multi-sensory therapy comprising a computer comprising an audio output and a screen, wherein the computer is configured to provide audio stimulus and visual stimulus, a motion chair, and an actuator coupled to the motion chair, wherein the actuator is configured to cause movement of the motion chair, wherein the motion of the motion chair is configured to provide tactile stimulus, vestibular stimulus and proprioceptive stimulus to a patient seated in the motion chair, wherein the stimuli provided by the computer is provided concurrently with the stimuli provided by the motion chair. In this embodiment, the audio stimulus may comprise music. Further, the audio stimulus may comprise a filtering routine having a first interval and a second interval, wherein during the second interval a first frequency range has been filtered from the audio stimulus. In this embodiment, the visual stimulus may comprise an animation having a substantially monochromatic background and a foreground figure disposed in the foreground.

In an embodiment, a system for providing multi-sensory therapy comprising a frame, an actuator supported by the frame and having a center of rotation, a chair coupled to the actuator, and a positioner supported by the frame, wherein the positioner is configured to position and support a computer secured to a support surface of the positioner, wherein the actuator is configured to cause three dimensional rotation of the chair about the center of rotation of the actuator. In this embodiment, the actuator may be configured to rotate the chair about the center of rotation along a first axis of rotation and a second axis of rotation, wherein the first axis of rotation is parallel to the chair and the second axis of rotation is perpendicular to the chair.

In an embodiment, a method for providing a multi-sensory therapy program comprising performing a diagnostic test on a patient, and performing ten hours of multi-sensory therapy on the patient over the course of five consecutive days, wherein two one hour sessions of multi-sensory therapy are performed on the patient on each consecutive day. In this embodiment, performing a diagnostic test on a patient may comprise performing a hearing test on the patient and procuring a writing sample from the patient.

In an embodiment, a method for providing a multi-sensory therapy session comprising disposing a patient on a chair in a reclining position, stimulating the patient with audio and visual stimuli via a computer, and concurrently stimulating the patient with vestibular, tactile and proprioceptive stimuli via motion of the chair. In this embodiment, stimulating the patient with audio stimulus may comprise (i) playing an audio stimulus composition and (ii) playing the audio stimulus composition with a first frequency range filtered from the audio stimulus composition. In this embodiment, stimulating the patient with visual stimulus may comprise (i) providing a visual animation having a substantially monochromatic background, (ii) inserting a foreground figure into the foreground of the animation, and (iii) removing the foreground figure from the foreground of the animation.

Embodiments described herein comprise a combination of features and characteristics intended to address various shortcomings associated with certain prior devices, systems, and methods. The various features and characteristics described above, as well as others, will be readily apparent to those skilled in the art upon reading the following detailed description, and by referring to the accompanying drawings.

BRIEF DESCRIPTION OF THE DRAWINGS

For a detailed description of exemplary embodiments, reference will now be made to the accompanying drawings in which.

DETAILED DESCRIPTION

In the drawings and description that follow, like parts are typically marked throughout the specification and drawings with the same reference numerals. The drawing figures are not necessarily to scale. Certain features of the invention may be shown exaggerated in scale or in somewhat schematic form and some details of conventional elements may not be shown in the interest of clarity and conciseness. The present disclosure is susceptible to embodiments of different forms. Specific embodiments are described in detail and are shown in the drawings, with the understanding that the present disclosure is to be considered an exemplification of the principles of the disclosure, and is not intended to limit the disclosure to that illustrated and described herein. It is to be fully recognized that the different teachings of the embodiments discussed below may be employed separately or in any suitable combination to produce desired results.

Unless otherwise specified, in the following discussion and in the claims, the terms "including" and "comprising" are used in an open-ended fashion, and thus should be interpreted to mean "including, but not limited to . . . ". Any use of any form of the terms "connect", "engage", "couple", "attach", or any other term describing an interaction between elements is not meant to limit the interaction to direct interaction between the elements and may also include indirect interaction between the elements described. The various characteristics mentioned above, as well as other features and characteristics described in more detail below, will be readily apparent to those skilled in the art upon reading the following detailed description of the embodiments, and by referring to the accompanying drawings.

The embodiments described herein include systems and methods for providing multi-sensory or sensory integration therapy. For instance, an embodiment of a system for providing multi-sensory therapy generally includes a motion chair for providing tactile, vestibular and proprioceptive stimuli and a computer having a screen and a speaker for providing visual and audio stimuli, respectively. Another embodiment of a system for providing multi-sensory therapy generally includes a frame for supporting a motion chair and an adjustable stand for supporting and positioning a computer.

In an embodiment, a method for providing a multi-sensory therapy program generally includes conducting approximately ten hours of multi-sensory therapy over five consecutive days, with two approximately one hour sessions conducted on each consecutive day. In another embodiment, a method for performing or conducting multi-sensory therapy generally includes providing vestibular, tactile, proprioceptive, audio and visual stimuli to the patient concurrently for the period of approximately an hour.

Figure 1:
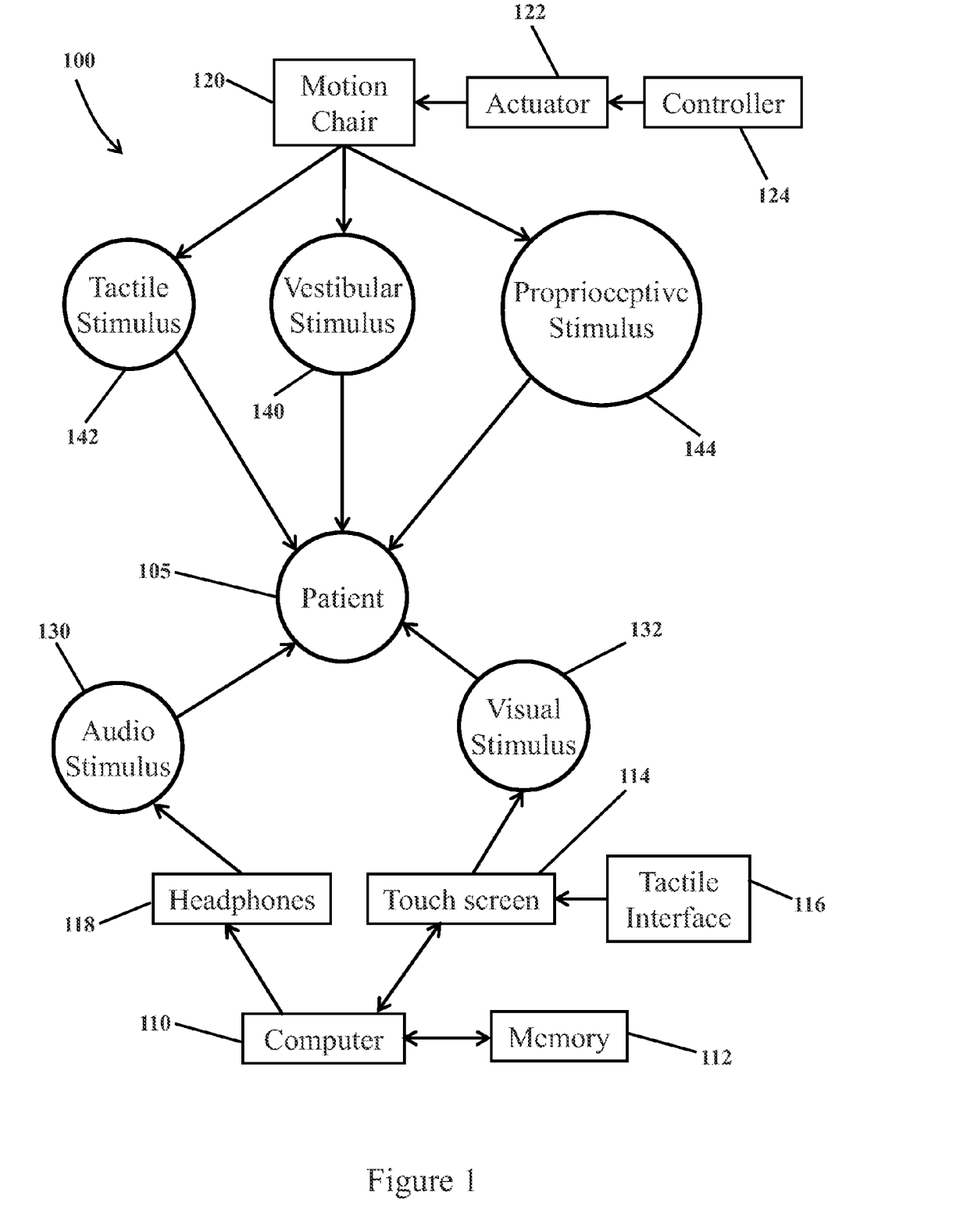
FIG. 1 is a block diagram of an embodiment of a multi-sensory therapy system in accordance with principles disclosed herein.

Referring initially to FIG. 1, an embodiment of a multi-therapy system 100 for treating a patient 105 includes a computer 100 having memory 112 and a touch screen 114 that provides a tactile interface 116 for providing input to the computer 110 and memory 112. The computer 110 also provides audio data stored in the memory 112 to a pair of stereo headphones 118 coupled to computer 110 for providing stereophonic audio stimulus 130 to the patient 105. The use of stereophonic headphones 118 allows for individual "right" and "left" stereo audio streams to be provided to the right and left ears of the patient 105. Visual stimulus 132 is provided via the touch screen 114 in conjunction with the audio stimuli 130.

The audio stimulus 130 provided by headphones 118 generally includes an audio stimulus composition in the form of a stream of music of either original or unfamiliar music that has been specially filtered for use in multi-sensory or sensory integration therapy. The filtering of the musical composition may follow a predetermined routine. Specifically, in an embodiment, varying frequency ranges are filtered out of the music over specific temporal intervals. For example, over a given span of several minutes of music, for a first interval the music may play as originally composed, followed by a second interval where a first particular frequency range has been filtered or cut from the music, followed by a third interval of unfiltered music, followed by a fourth interval of music where a second frequency range has been filtered from the music, etc. In an embodiment, each interval may span approximately between 10-30 seconds. Thus, the filtering methodology performed on the auditory stimulus or music is configured to intuitively direct the patient's 105 attention towards piecing together the originally composed musical composition from the filtered music. Moreover, the use of original or unfamiliar music may enhance this phenomenon by making the sequence of music unpredictable to the patient 105. The use of popular music may not have such an effect as the patient 105 may already have knowledge of the music used prior to the therapy session. While in this embodiment filtering of frequency ranges has been described with regard to music, in other embodiments other forms of audio stimulus may be used.

The visual stimulus 132 provided by the touch screen 114 of the computer 110 in conjunction with the audio stimulus 130 provided by the headphones 118. In an embodiment, the visual stimulus 132 provided to the patient 105 generally includes a computer generated animation having a substantially monochromatic background with a geometric or foreground figure disposed in the foreground, located at the approximate center of the touch screen 114. In this embodiment, the monochromatic background is a dark or black background and the foreground figure is a circle having a solid red color. At the beginning of the animation (i.e., at the beginning of the therapy session), the touch screen 114 is entirely dark, with the foreground circle appearing later in a gradual "fade in" animation. Later in the animation, the circle gradually "fades out" of the foreground, leaving a black background. Over the course of the animation (i.e., over the course of the therapy session), the circle completes many periodic "fade in" and "fade out" cycles at a given frequency. For instance, in an embodiment, a "fade in" and "fade out" cycle may take place over approximately 15-30 seconds. While in this embodiment the foreground figure is a red circle, in other embodiments the foreground figure may take other colors and geometric forms. In other embodiments, the foreground figure may be monochromatic or multi-colored. Also, the "fade in" and "fade out" cycle may take place over different lengths of time. Moreover, the foreground figure may appear and be removed from the foreground of the animation in ways differently than a "fade in" and "fade out" animation. For instance, the foreground figure may suddenly appear and disappear from the foreground, or another form of animation may be used to introduce and remove the foreground figure from the animation.

The audio 130 and visual 132 stimuli generated by the computer 110 provides the patient 105 with two different sensory modalities. A third modality, sensorimotor, is provided by the motion chair 120. The chair 120 includes an actuator for providing motion to the chair 120 and is controlled by a controller 124. In this embodiment, controller 124 includes an "on" and an "off" configuration. When switched into the "on" configuration, a timer of the controller 124 is activated, thus allowing the actuator 122 to remain on until the timer has expired, at which point the actuator 122 is turned off. In an embodiment, the timer of the controller 124 is set to expire in the period of approximately an hour. As will be discussed further herein, the actuator 122 is configured to provide motion to the table 120 such that vestibular 140, tactile 142 and proprioceptive 144 stimuli is provided to the patient 105 concurrently with the audio 130 and visual 132 stimuli over the course of the therapy session.

Figure 2A:
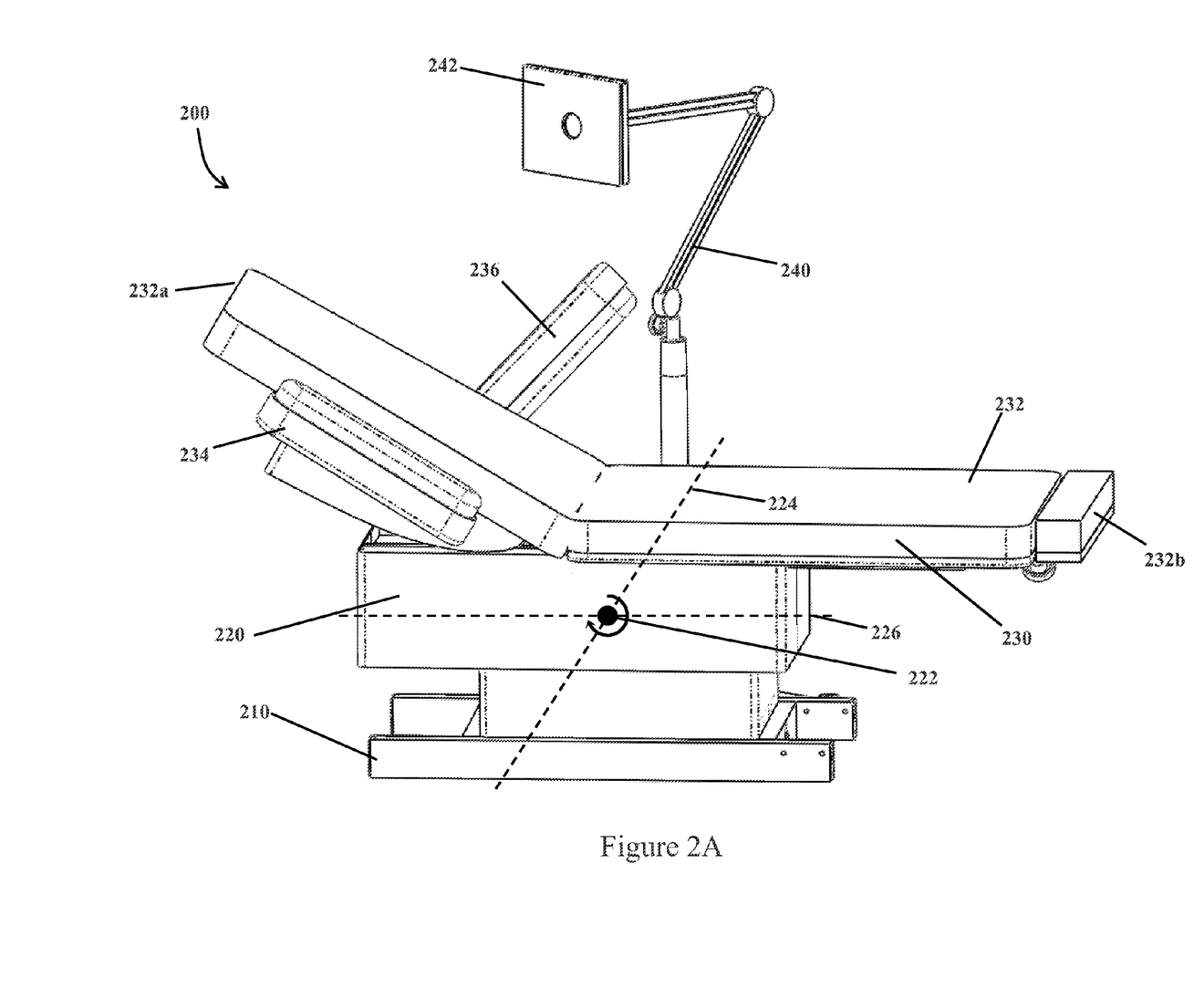
FIGS. 2A-2C are perspective views of an embodiment of a multi-sensory therapy system in accordance with principles disclosed herein.
Figure 2B:
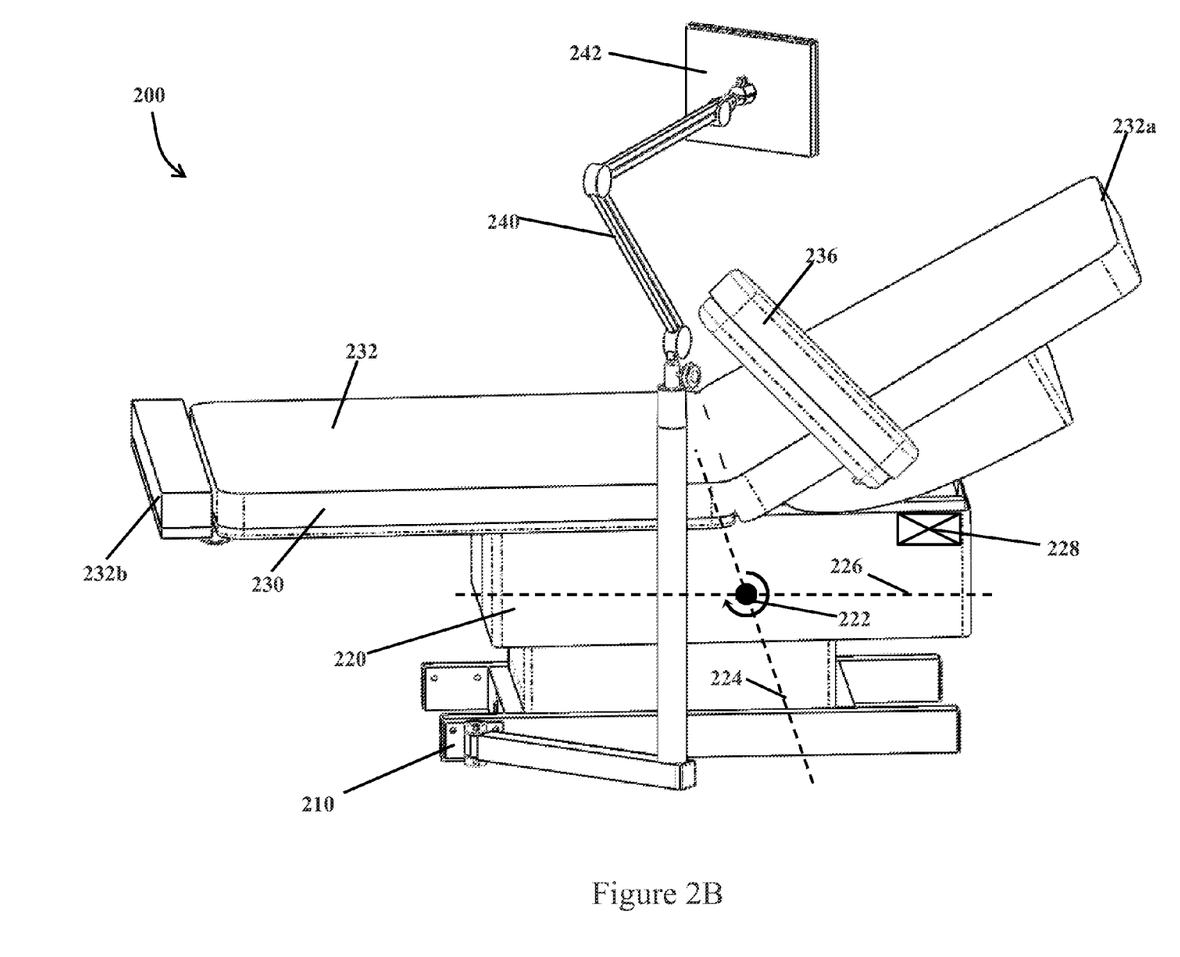
Figure 2C:
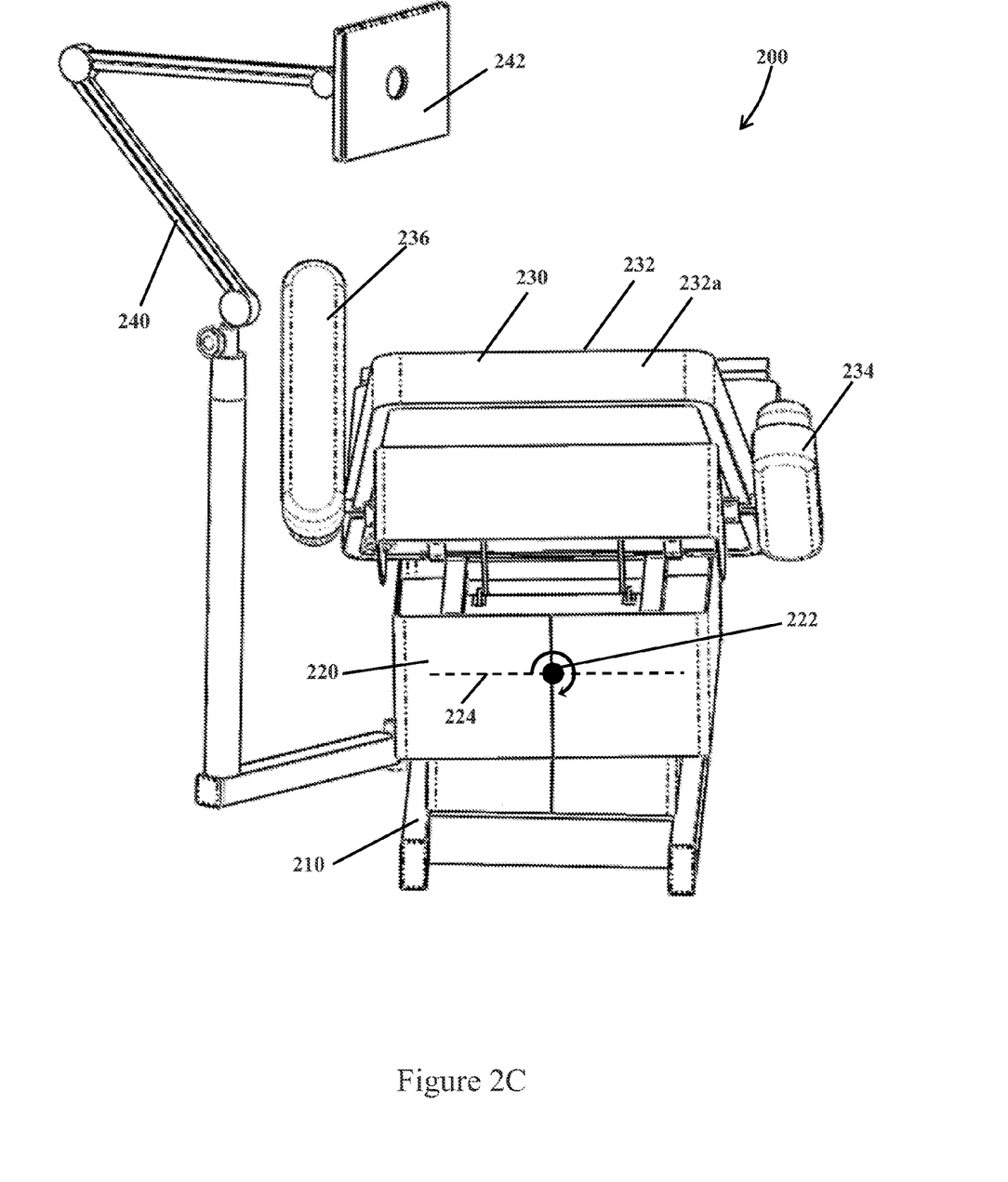

Referring to FIGS. 2A-2C, an embodiment of a multi-therapy system 200 includes a frame 210 supporting an actuator 220, a chair 230 and a positioner 240. The chair 230 includes an inclined support surface 232 configured to support the body of a patient (e.g., patient 105 of system 100), a right armrest 234 and a left armrest 236. Also, the support surface 232 includes a first end 232 proximal to the patient's head and a second end 232b proximal to the patient's feet. The positioner 240 includes a support 242 for securing a computer (e.g., computer 100) having a touch screen and an audio output. The positioner 240 is configured to allow the support 242 to be positioned in a number of different positions relative to the support surface 232 of chair 230. Thus, a computer secured to support 242 may be precisely positioned relative to the head of a patient seated in chair 230. In an embodiment, during a multi-sensory therapy session using system 200 the support 242 is positioned approximately 14" from the face of a patient seated in chair 230.

The actuator 220 is configured to provide motion to the chair 230 and includes a center of rotation (COR) 222 having a first axis of rotation 224 that is parallel with the chair 230 and a second axis of rotation 226 that is perpendicular to the chair 230. The chair 230 may be rotated about the first axis of rotation 224 (i.e., rotation in the direction of either end 232a or end 232b) or about the second axis of rotation 226 (i.e., rotation in the direction of either armrest 234 or armrest 236). Thus, instead of a simple rocking motion, a three dimensional rolling motion may be created of the chair 230 by rotation about first axis 224 and the second axis 226. The rolling motion created by such three dimensional rotation allows for the creation of vestibular, tactile and proprioceptive stimuli in a patient seated in chair 230 during actuation of the chair by actuator 220, as the patient is rocked and rolled from side-to-side. Referring momentarily to FIG. 1 again, actuator 220 and chair 230 may be used for actuator 122 and chair 120 in system 100. Moreover, positioner 240 and support 242 may be used to secure computer 100 of system 100.

In an embodiment, a clockwise rolling motion of chair 230 is created by actuator 220. This may be accomplished by first rotating chair 230 about first axis 224 in a first direction towards end 232b (i.e., rotated clockwise in the first direction 224). Following this rotation, chair 230 is rotated about second axis 226 in a first direction towards right armrest 234. Next, chair 230 is rotated again about first axis 224 in a second direction towards end 232a of surface 232. Last, chair 230 is rotated again about second axis 226 in a second direction towards left armrest 236. Following a complete clockwise rotation chair 230, the motion of chair 230 may be reversed and a counterclockwise rotation of chair 230 is conducted, resulting in a "figure eight" motion of the chair 230, enhancing the stimuli provided to the patient. In order to control the actuation of actuator 220, a controller 228 is provided (FIG. 2B).

Figure 3:
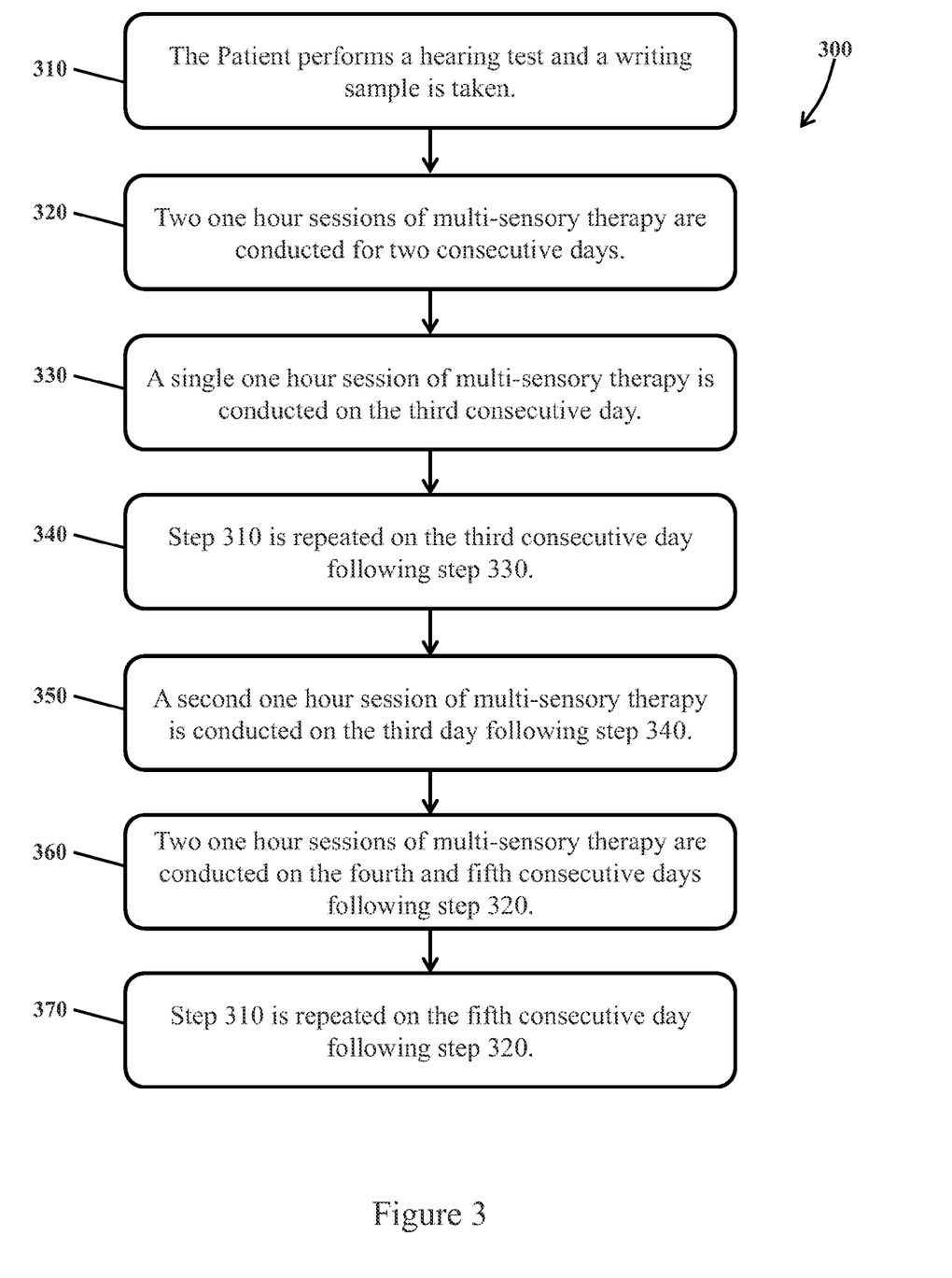
FIG. 3 is a flow chart of an embodiment of a method for conducting a multi-sensory therapy program in accordance with principles disclosed herein.

Having described systems for use in multi-sensory therapy, methods for conducting multi-sensory therapy via the previously discussed systems will now be described. Referring now to FIG. 3, a method of conducting a multi-sensory therapy program 300 begins at step 310 by performing a hearing test and procuring a writing sample from the patient. At step 320, two one hour sessions of multi-sensory therapy are conducted for two consecutive days. The multi-sensory therapy sessions performed at step 320 may be performed via systems 100 and/or 200. At step 330, a single one hour session of multi-sensory therapy is conducted on the third consecutive day. At step 340, step 310 is repeated on the third consecutive day following step 330. At step 350, a second one hour session of multi-sensory therapy (e.g., via systems 100 and/or 200) is conducted on the third day following step 340. At step 360, two one hour sessions of the multi-sensory therapy are conducted on the fourth and fifth consecutive days following step 320. Last, at step 370, step 310 is repeated on the fifth consecutive day following step 320.

Figure 4:
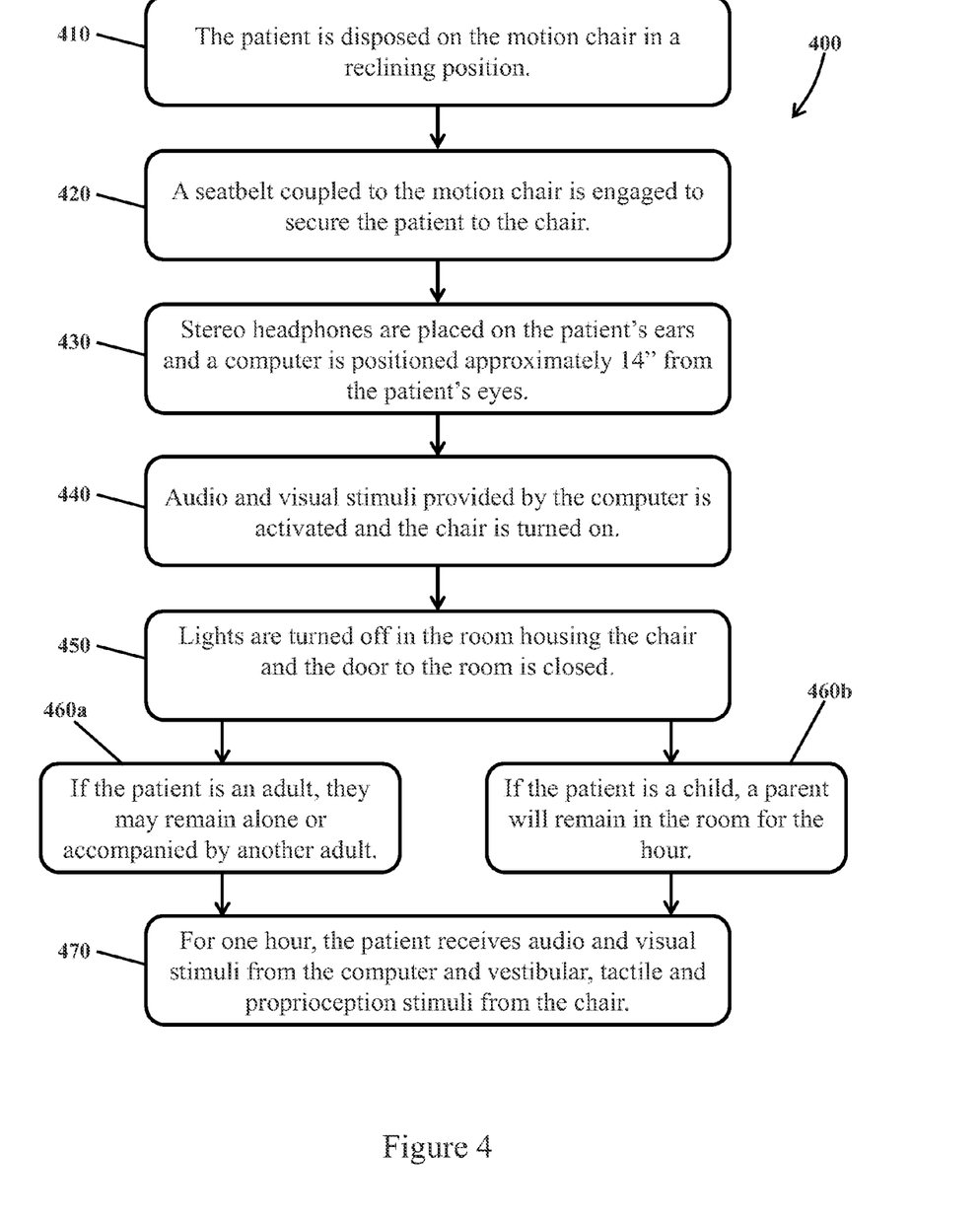
FIG. 4 is a flow chart of an embodiment of a method for conducting multi-sensory therapy in accordance with principles disclosed herein.

Referring now to FIG. 4, a method of conducting a multi-therapy session (e.g., the multi-therapy sessions conducted in method 300), begins at step 410 where the patient (e.g., patient 105) is disposed on the motion chair (e.g., motion chair 230) in a reclining position. At step 420, a seatbelt coupled to the motion chair is engaged to secure the patient to the chair. At step 430 stereo headphones (e.g., headphones 118) are placed on the patient's ears and a computer (e.g., computer 110) is positioned approximately 14" from the patient's eyes. At step 440, audio and visual stimuli (e.g., stimuli 130 and 132) provided by the computer is activated and the chair is turned on (e.g., via actuator 220 and controller 228). At step 450, lights are turned off in the room housing the chair and the door to the room is closed. Following step 450, if the patient is an adult, then step 460a is conducted, where the patient may remain alone or accompanied by another adult. However, if the patient is a child, then step 450 is followed by step 460b, where a parent will remain in the room with the child for the hour. Last, at step 470, for one hour, the patient receives audio and visual stimuli (e.g., stimuli 130 and 132) from the computer and vestibular, tactile and proprioception stimuli (e.g., stimuli 140, 142 and 144) from the chair. Moreover, the method 400 may be conducted via the multi-therapy systems 100 and/or 200 described in FIGS. 1-2C. Once the audio and visual stimulus step has completed, a light may be illuminated from underneath the chair to allow the patient to see within the room.

Using the systems and methods disclosed herein, a patient may receive stimuli to at least five different senses (e.g., audio, visual, vestibular, tactile and proprioception) in a coordinated manner such that the patient's sensory systems are re-educated in an efficient and optimized way. The centralized processing unit, such as the computer or iPad, coordinates with the motion chair such that the patient receives sensory therapy in a passive but assistive manner. In this way, the tactile, vestibular, proprioceptive, auditory and visual sensory systems are stimulated concurrently, and thus, are fully integrated. Therefore, by fully integrating each of the aforementioned senses the systems and methods disclosed herein offer sensory integration therapy that is more effective and intensive in beneficially treating SPD and other disorders. Further, the intense stimulation and full integration of sensory stimuli offered by the systems and methods disclosed herein also reduces the overall time duration necessary of treatment required in order to provide beneficial and effective therapy directed towards SPD or other disorders. For instance, by stimulating each of the senses concurrently, the overall time the patient is exposed to stimulus as part of providing a beneficial therapeutic effect with regard to SPD or other disorders may be reduced The above discussion is meant to be illustrative of the principles and various embodiments of the present disclosure. While certain embodiments have been shown and described, modifications thereof can be made by one skilled in the art without departing from the spirit and teachings of the disclosure. The embodiments described herein are exemplary only, and are not limiting. Accordingly, the scope of protection is not limited by the description set out above, but is only limited by the claims which follow, that scope including all equivalents of the subject matter of the claims.

What is claimed is:

1. A method for providing a multi-sensory therapy session comprising:
    disposing a patient on a chair in a reclining position;
    stimulating the patient with an audio stimulus and a visual stimulus via a computer; and
    concurrently stimulating the patient with a vestibular stimulus, a tactile stimulus, and a proprioceptive stimulus via a motion of the chair;
    wherein stimulating the patient via motion of the chair comprises:
        (i) rotating the chair about a first axis of rotation in a first direction
        (ii) rotating the chair about a second axis of rotation in a first direction following (i);
        (iii) rotating the chair about the first axis of rotation in a second direction opposite the first direction following (ii); and
        (iv) rotating the chair about the second axis of rotation in a second direction opposite the first direction following (iii).

2. The method of claim 1, wherein the computer stimulation and the chair stimulation are coordinated to simultaneously affect multiple related senses of the patient.

3. The method of claim 1, wherein stimulating the patient with the audio stimulus comprises:
    (a) playing an audio stimulus composition; and
    (b) playing the audio stimulus composition with a first frequency range filtered from the audio stimulus composition following (a).

4. The method of claim 3, further comprising:
    (c) playing the audio stimulus composition following (b); and
    (d) playing the audio stimulus composition with a second frequency range filtered from the audio stimulus composition following (c), the second frequency range differing from the first frequency range.

5. The method of claim 1, wherein the stimulating the patient with the visual stimulus comprises:
    (i) providing a visual animation having a substantially monochromatic background;
    (ii) inserting a foreground figure into the foreground of the animation; and
    (iii) removing the foreground figure from the foreground of the animation.

6. The method of claim 1, further comprising:
    (v) rotating the chair about the first axis of rotation in the first direction following (iv);
    (vi) rotating the chair about the second axis of rotation in the second direction following (v);
    (vii) rotating the chair about the first axis of rotation in the second direction following (vi); and
    (viii) rotating the chair about the second axis of rotation in the first direction following (vii).

* * * * *